(12) United States Patent
Mathies

(10) Patent No.: US 9,592,125 B2
(45) Date of Patent: Mar. 14, 2017

(54) IN SITU SYSTEM FOR INTRA-ARTICULAR CHONDRAL AND OSSEOUS TISSUE REPAIR

(75) Inventor: Burkhard Mathies, Givrins (CH)

(73) Assignee: Laboratoire Medidom S.A., Geneva (CH)

( * ) Notice: Subject to any disclaimer, the term of this patent is extended or adjusted under 35 U.S.C. 154(b) by 603 days.

(21) Appl. No.: 11/962,228

(22) Filed: Dec. 21, 2007

(65) Prior Publication Data

US 2008/0154370 A1 Jun. 26, 2008

Related U.S. Application Data

(60) Provisional application No. 60/871,554, filed on Dec. 22, 2006.

(51) Int. Cl.
*A61F 2/30* (2006.01)
*A61L 27/20* (2006.01)
*A61L 27/58* (2006.01)

(52) U.S. Cl.
CPC .......... *A61F 2/30756* (2013.01); *A61L 27/20* (2013.01); *A61L 27/58* (2013.01);
(Continued)

(58) Field of Classification Search
CPC ................ A61F 13/00; A61F 13/00029; A61F 13/00012; A61F 13/00038; A61F 2/30756;
(Continued)

(56) References Cited

U.S. PATENT DOCUMENTS

| 4,350,629 A | 9/1982 | Yannas et al. ............. 260/123.7 |
| 4,703,108 A | 10/1987 | Silver et al. .................. 530/356 |

(Continued)

FOREIGN PATENT DOCUMENTS

| AU | 2002362932 | 6/2008 |
| CA | 2 353 409 A1 | 6/2000 |

(Continued)

OTHER PUBLICATIONS

Euflexxa. Product Information [online], BTG Technology General, Israel Ltd., May 30, 2014 [retrieved May 30, 2014]. Retrieved from the Internet <URL: http://www.btgil.com/products/euflexxa/>.*

(Continued)

*Primary Examiner* — Christopher D Prone
*Assistant Examiner* — Rokhaya Diop
(74) *Attorney, Agent, or Firm* — Seed IP Law Group PLLC

(57) ABSTRACT

Disclosed is a device and method which provide a surgical therapy for in situ treatment and repair of intra-articular cartilage lesions and/or defects. The device is an implantable laminate cartilage repair patch which is bio-compatible and physiologically absorbable. The cartilage repair patch has a first outer cell occlusive layer; a second outer, cell porous layer adapted to be disposed proximate a subchondral bone wound site; and a cartilagenic matrix disposed between the first and second layers. The cartilagenic matrix is a sink for diffusion of autologous stem cells and includes chemical components promoting generation of hyaline-like cartilage in the presence of the autologous stem cells. The method of the present invention provides the autologous compositions, which when used in combination with the repair patch provides a therapeutic system to regenerate replacement hyaline-like intraarticular cartilage.

10 Claims, 6 Drawing Sheets

(52) U.S. Cl.
CPC ............... *A61F 2002/30677* (2013.01); *A61F 2002/30766* (2013.01); *A61F 2002/30971* (2013.01); *A61F 2310/00365* (2013.01)

(58) Field of Classification Search
CPC .. A61F 2002/30757; A61F 2002/30759; A61F 2002/30761; A61F 2002/30762; A61F 2002/30764; A61F 2002/30766; A61F 2/0063; A61F 2002/30677; A61F 2002/30971; A61F 2310/00365; A61L 27/54; A61L 27/58; A61L 27/3852; A61L 27/3633; A61L 27/3604; A61L 27/20
USPC ................... 623/11.11, 14.12, 23.72–23.76; 424/423–424
See application file for complete search history.

(56) References Cited

U.S. PATENT DOCUMENTS

| | | | |
|---|---|---|---|
| 4,837,024 A | 6/1989 | Michaeli | 424/446 |
| 4,880,429 A * | 11/1989 | Stone | 623/14.12 |
| 5,067,964 A * | 11/1991 | Richmond et al. | 623/14.12 |
| 5,397,353 A | 3/1995 | Oliver et al. | 623/11 |
| 5,567,806 A | 10/1996 | Abdul-Malak et al. | 530/356 |
| 5,681,353 A | 10/1997 | Li et al. | 623/18 |
| 6,042,610 A * | 3/2000 | Li et al. | 623/20.32 |
| 6,080,194 A * | 6/2000 | Pachence et al. | 623/23.76 |
| 6,352,558 B1 * | 3/2002 | Spector | 623/18.11 |
| 6,596,304 B1 | 7/2003 | Bayon et al. | 424/444 |
| 6,629,997 B2 * | 10/2003 | Mansmann | 623/14.12 |
| 6,737,072 B1 | 5/2004 | Angele et al. | |
| 6,989,034 B2 * | 1/2006 | Hammer et al. | 623/23.72 |
| 7,141,072 B2 * | 11/2006 | Geistlich et al. | 623/23.74 |
| 7,217,294 B2 | 5/2007 | Kusanagi et al. | 623/18.11 |
| 7,476,250 B1 | 1/2009 | Mansmann | 623/14.12 |
| 2002/0025921 A1 | 2/2002 | Petito et al. | 514/2 |
| 2002/0028233 A1 | 3/2002 | Dimitrijevich | 424/447 |
| 2002/0045940 A1 * | 4/2002 | Giannetti et al. | 623/11.11 |
| 2002/0103542 A1 | 8/2002 | Bilbo | 623/23.72 |
| 2002/0111576 A1 | 8/2002 | Greene et al. | 602/42 |
| 2002/0122790 A1 | 9/2002 | Hunziker | 424/93.7 |
| 2002/0151985 A1 | 10/2002 | Kuberasampath et al. | 623/23.58 |
| 2002/0151986 A1 * | 10/2002 | Asculai et al. | 623/23.75 |
| 2002/0173806 A1 | 11/2002 | Giannetti et al. | 606/151 |
| 2002/0183845 A1 * | 12/2002 | Mansmann | 623/13.11 |
| 2002/0183858 A1 * | 12/2002 | Contiliano et al. | 623/23.76 |
| 2003/0004578 A1 * | 1/2003 | Brown et al. | 623/23.72 |
| 2003/0036801 A1 * | 2/2003 | Schwartz et al. | 623/23.63 |
| 2003/0039695 A1 | 2/2003 | Geistlich et al. | |
| 2003/0078617 A1 * | 4/2003 | Schwartz et al. | 606/230 |
| 2003/0114061 A1 * | 6/2003 | Matsuda et al. | 442/123 |
| 2003/0118560 A1 | 6/2003 | Kelly et al. | 424/93.7 |
| 2003/0143207 A1 * | 7/2003 | Livesey et al. | 424/93.7 |
| 2003/0187515 A1 * | 10/2003 | Hariri et al. | 623/23.72 |
| 2003/0219429 A1 | 11/2003 | Budny | 424/94.63 |
| 2003/0220700 A1 * | 11/2003 | Hammer et al. | 623/23.58 |
| 2003/0225355 A1 | 12/2003 | Butler | 602/48 |
| 2004/0097612 A1 | 5/2004 | Rosenberg et al. | 523/113 |
| 2004/0141945 A1 | 7/2004 | Yura et al. | 424/85.1 |
| 2004/0224022 A1 | 11/2004 | Spiro et al. | 424/484 |
| 2005/0043814 A1 * | 2/2005 | Kusanagi et al. | 623/23.58 |
| 2005/0125077 A1 * | 6/2005 | Harmon et al. | 623/23.72 |
| 2005/0186283 A1 | 8/2005 | Geistlich et al. | |
| 2005/0208114 A1 | 9/2005 | Petito et al. | 424/445 |
| 2005/0209705 A1 * | 9/2005 | Niederauer et al. | 623/23.63 |
| 2005/0232967 A1 * | 10/2005 | Kladakis et al. | 424/423 |
| 2005/0232979 A1 | 10/2005 | Shoshan | 424/445 |
| 2005/0281856 A1 | 12/2005 | McGlohorn et al. | 424/423 |
| 2006/0008905 A1 | 1/2006 | Mattern et al. | 435/395 |
| 2006/0083730 A1 | 4/2006 | Kusanagi et al. | 424/94.1 |
| 2006/0100138 A1 | 5/2006 | Olsen et al. | 514/8 |
| 2006/0241756 A1 * | 10/2006 | Fritz et al. | 623/14.12 |
| 2008/0119947 A1 * | 5/2008 | Huckle et al. | 623/23.72 |
| 2008/0125863 A1 * | 5/2008 | McKay | 623/11.11 |
| 2008/0167716 A1 * | 7/2008 | Schwartz et al. | 623/11.11 |
| 2008/0183300 A1 * | 7/2008 | Seedhom et al. | 623/23.76 |

FOREIGN PATENT DOCUMENTS

| | | |
|---|---|---|
| EP | 0 514 691 | 11/1992 |
| EP | 0 544 259 | 6/1993 |
| EP | 0 640 647 | 9/1996 |
| EP | 0 781 564 | 7/1997 |
| EP | 0 913 162 | 5/1999 |
| EP | 1 022 031 | 7/2000 |
| EP | 1 252 903 | 10/2002 |
| EP | 1 283 063 | 2/2003 |
| EP | 1 313 421 | 5/2003 |
| EP | 1 319 415 | 6/2003 |
| EP | 0 808 142 | 8/2003 |
| EP | 1 338 291 | 8/2003 |
| EP | 0 810 888 | 4/2004 |
| EP | 1 452 153 | 9/2004 |
| EP | 1 023 091 | 1/2005 |
| EP | 1 493 404 | 1/2005 |
| EP | 1 506 790 | 2/2005 |
| EP | 0 738 161 | 12/2005 |
| EP | 1 623 681 | 2/2006 |
| EP | 1 085 842 | 3/2006 |
| EP | 1 255 577 | 3/2006 |
| EP | 1 676 592 | 7/2006 |
| EP | 1 345 635 | 1/2007 |
| EP | 1 135 177 | 12/2007 |
| EP | 1 438 081 | 3/2008 |
| EP | 1 935 438 | 6/2008 |
| EP | 1 735 022 | 7/2009 |
| JP | 2000-514698 A | 11/2000 |
| JP | 2001-517493 A | 10/2001 |
| JP | 2001-519210 A | 10/2001 |
| JP | 2002-531182 A | 9/2002 |
| JP | 2003-160506 A | 6/2003 |
| JP | 2003-245338 A | 9/2003 |
| JP | 2006-501879 A | 1/2006 |
| WO | 96/24310 | 8/1996 |
| WO | 97/22372 | 6/1997 |
| WO | 98/31345 A1 | 7/1998 |
| WO | 99/15210 A3 | 4/1999 |
| WO | 99/19005 A1 | 4/1999 |
| WO | 00/16822 | 3/2000 |
| WO | 00/48550 | 8/2000 |
| WO | 01/66159 | 9/2001 |
| WO | 01/70293 | 9/2001 |
| WO | 02/17713 | 3/2002 |
| WO | 02/45767 | 6/2002 |
| WO | 03/072157 | 9/2003 |
| WO | 2004/008997 A1 | 1/2004 |
| WO | 2004/078120 | 9/2004 |
| WO | 2005/085293 A1 | 9/2005 |
| WO | 2007/020449 | 2/2007 |
| WO | 2007/049125 | 5/2007 |
| WO | 2007/070617 | 6/2007 |
| WO | 2007/071164 | 6/2007 |
| WO | 2008/017858 | 2/2008 |
| WO | 2008/067085 | 6/2008 |
| WO | 2008/105791 | 9/2008 |
| WO | 2009/048930 | 4/2009 |
| WO | 2009/076391 | 6/2009 |

OTHER PUBLICATIONS

Kramer et al., "In vivo matrix-guided human mesenchymal stem cells", Cell. Mol. Life Sci. 63 (2006) 616-626, Birkhäuser Verlag, Basel.

International Search Report, mailed Mar. 19, 2009, for PCT/IB2007/004067, 2 pages.

Nishimori et al., "Repair of chronic osteochondral defects in the rat," *The Journal of Bone and Joint Surgery* 88(9):1236-1244, Sep. 2006.

Saw et al., "Articular Cartilage Regeneration With Autologous Peripheral Blood Progenitor Cells and Hyaluronic Acid After

(56) References Cited

OTHER PUBLICATIONS

Arthroscopic Subchondral Drilling: A Report of 5 Cases With Histology," *Arthroscopy: The Journal of Arthroscopic and Related Surgery* 27(4):493-506, Apr. 2011.
"Xenoderm," retrieved Jul. 12, 2012, from http://biometica-ag.tradenote.net/product/422454-Xenoderm.html, 4 pages.

* cited by examiner

IN SITU SYSTEM FOR INTRA-ARTICULAR CHONDRAL AND OSSEOUS TISSUE REPAIR

The present application claims the benefit of prior filed U.S. provisional patent application Ser. No. 60/871,554 filed 22 Dec. 2006, the content of which is incorporated herein by reference.

FIELD OF THE INVENTION

The present invention is in the field of bioaffecting and body treating compositions having components associated as layers or impregnated matrix (believed to be classified in Class 424/400). Specifically, the present invention relates to compositions in a physical form to adapt for surgical implanting or inserting in the living body (believed to be classified in Class 424/400; 423). More specifically, the present invention relates to such compositions in which the surgical implant or material is errodable, resorbable, or dissolving (believed to be classified in Class 424/400; 423; 426).

BACKGROUND OF THE INVENTION

One of the goals of medicine, including the surgical arts, is the recovery of health that has been lost, whether the loss occurred as a result of injury or disease. In the surgical arts, ever more effective treatment strategies for addressing cartilage defects are being sought. Such defects in joints (intra-articular) can result from a number of different causes, including trauma and diseases such as osteoarthritis. The hyalinic articular cartilage is a specialized connective tissue in the body with weight bearing and shock absorbing properties and functions. Injury to or loss of this specialized connective tissue in a joint leads to pain and impaired joint function.

Although the hyalinic articular cartilage does have some self-repairing capabilities, these are very limited. Therefore, the orthopedic surgical arts field has been motivated to develop therapies which replace or promote regeneration of damaged joint cartilage. This is in response to the large number of joint injuries that occur yearly, and the increasing number of the elderly with joint problems. Typically, these therapies are merely surgical methods which debride and mechanically repair the injury, with or without the addition to the injury site of an active composition to promote healing or to prevent inflammation/infection.

More recently, the field has tried bio-engineering influenced therapies which added a structural composition to the injury, such as autologous tissue grafts, in order to promote appropriate healing. However, osteochondral injuries, which are a combination lesion of bone and cartilage, represent therapeutic challenges, and fully satisfactory therapeutic compositions and treatment methods are still lacking in many cases. For example, certain surgical procedures for osteochondritis dissecans using autologous chondrocyte transplantation require extensive periods for the cell cultivation and growth aspect and multiple surgeries. Additionally, these therapies often result in the propagation of a fibrocartilaginous replacement tissue, which is a poor substitute for hyaline articular cartilage. See J. Kramer et al., Cell. Mol. Life Sci., 63, 616-626 (2006).

Therefore, it would be beneficial in the field to have alternative treatment for osteochondral injuries that do not require cell culture, and do not result in propagation of a fibrocartilaginous replacement tissue at the injury site. It would be even more advantageous if the resultant replacement tissue was appreciably representative of natural hyalinelike articular cartilage.

SUMMARY OF THE INVENTION

The present invention is an in situ healing/tissue growth promoting system and method, utilizing natural, non-human Hyaluronic Acid and 5 autologous mesenchymal stem cells to regenerate intra-articular cartilage lesions. More specifically, a system and method is provided that can stimulate growth of hyaline-like cartilage in situ to correct intra-articular cartilage defects. To this end, the present system comprises a medical cartilage repair patch consisting of a natural composite 10 Hyaluronic Acid and collagen fiber matrix additionally embedded with growth hormones and/or growth factors, and Diacerein and/or Rhein compositions. The system utilizes autologous mesenchymal stem-cells obtained through micro-fracture of the subchondral bone during installation of the cartilage repair patch as a component of the system to accomplish chondral and osseous tissue engineering in intra-articular defects.

The implantable laminate cartilage repair patch of the present invention is a surgical device that is bio-compatible and physiologically absorbable for in situ cartilage repair in intra-articular lesions. The cartilage repair patch is a laminate or multi-layered device. The device has a basement or bottom layer which is adapted to be disposed adjacent the bone site to be treated. This layer is "cell-porous" in that it allows the migration of cells from the wound site to pass through the layer. On top of and closely associated with the basement layer is a carlagenic matrix layer. The cartilagenic matrix is a collagenous layer and is a sink for the diffusion of autologous stem cells and other blood components at the wound site. The matrix layer includes chemical components which promote the generation of hyaline-like cartilage in the presence of the autologous stem cells. Also optionally, the top layer may be occlusive to one degree or another, for example, not allow cells to pass through, but allowing other small things, like water, gas and small molecules to pass through. All of these elements and features in combination provide the flexible, bio-compatible materials which are physiologically absorbable laminate cartilage repair patch of the present invention.

DETAILED DESCRIPTION OF THE INVENTION

Figure 1:
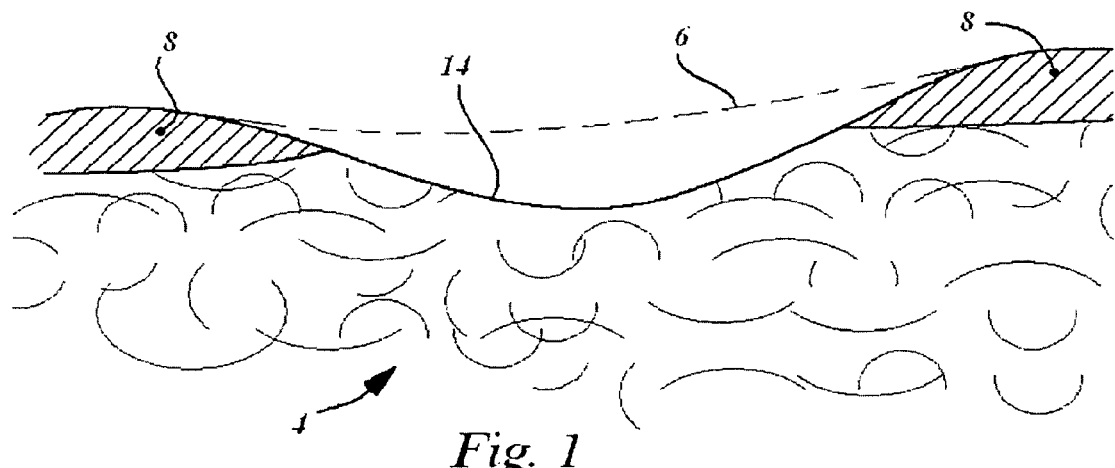
FIG. 1 is a cross-sectional view of subehondral bone showing a chondral/osteo-chondral lesion where a section of cartilage covering the osseous portion of the bone is missing.

Referring now to the drawings, the details of preferred embodiments of the present invention are graphically and schematically illustrated. Like elements in the drawings are represented by like numbers, and any similar elements are represented by like numbers with a different lower case letter suffix.

As shown in FIG. 1, one of the problems faced in this field is how to promote regeneration of a cartilaginous tissue at the defect or wound site (cartilage lesion) 6 that is as close as possible to the natural cartilage 8 proximate the site, or as otherwise would have covered the subchondral bone 4 at the site 6. This is particularly challenging at wound sites where the lesion involve both cartilage and bone.

As shown in FIGS. 2A to 2E, the present invention is an implantable cartilage repair patch 10 that is bio-compatible and physiologically absorbable, and that functions in situ to promote the regeneration of cartilage in intra-articular chondral or osteo-chondral lesions 6 (see FIG. 1). The present cartilage repair patch 10 is a sterilizeable, flexible laminate 12 that can be implanted at a wound site 6 and act to promote the generation of hyaline-like cartilage. The objective of the cartilage repair patch 10 is to stimulate growth of hyaline-like cartilage in-situ following arthroscopic or open surgical application of the cartilage repair patch 10 in patients with chondral or osteo-chondral damage. An additional object is that the cartilage repair patch 10 is biodegradable through the interaction of its constituents with collagenase and other proteases and will be reabsorbed and disappear over time.

The laminate 12 of the cartilage repair patch 10 is constructed completely of materials that are both bio-compatible and physiologically absorbable, so that the cartilage repair patch can be implanted indwelling in a patient and disappear from the implantation site over time. In one embodiment, the cartilage repair patch laminate 12 has a first top (optionally occlusive) layer 16, and a second bottom or basement porous layer 22. See FIGS. 2A to 2C. In another preferred embodiment, the cartilage repair patch laminate 12 is only two layers: a basement layer 22 and a matrix layer 30. See FIGS. 2D and 2E. The basement layer is intended to be interfaced with the surface of the bone at the wound site 6. Both of the basement layer 22 and the top layer 16 are made of sheet collagen (see Angele et al., U.S. Pat. No. 6,737,072. The content of which is incorporated herein by reference). An example of a satisfactory commercially available source of sheet collagen is: XENODERM™, Biometica AG, Switzerland. Disposed on the porous basement layer 22 is a cartilagenic matrix layer 30. The cartilagenic matrix layer 30 provides a collagenous substrate in which to entrap mesenchymal stem-cells, and a cell growth support medium on which they will grow and differentiate into chondrocytes in presence of the other natural components of the matrix layer 30.

Figure 2A:
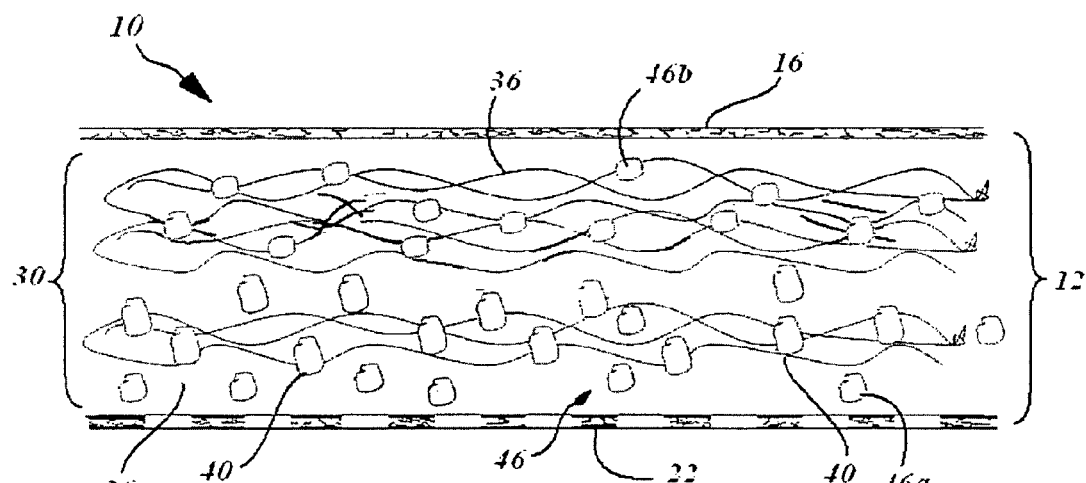
FIG. 2A is a cross-sectional side view of the sterilizeable, flexible laminate wound cartilage repair patch of the present invention, detailing the composition of the matrix of the patch wherein the collagen and the Hyaluronic Acid are disposed as fibers.
Figure 2B:
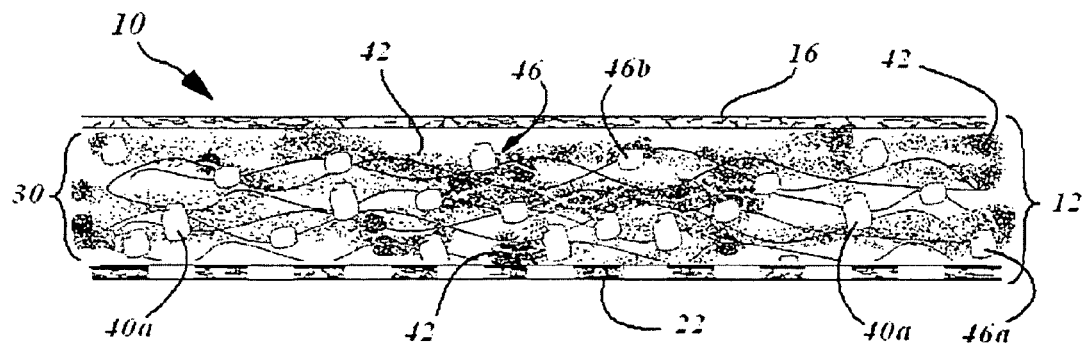
FIG. 2B is a cross-sectional side view of the sterilizeable, flexible laminate wound cartilage repair patch of the present invention, detailing the composition of the inner matrix of the patch, wherein the collagen is disposed as fibers and the Hyaluronic Acid is disposed as a cream suspension or as a viscoelastic solution.
Figure 2C:
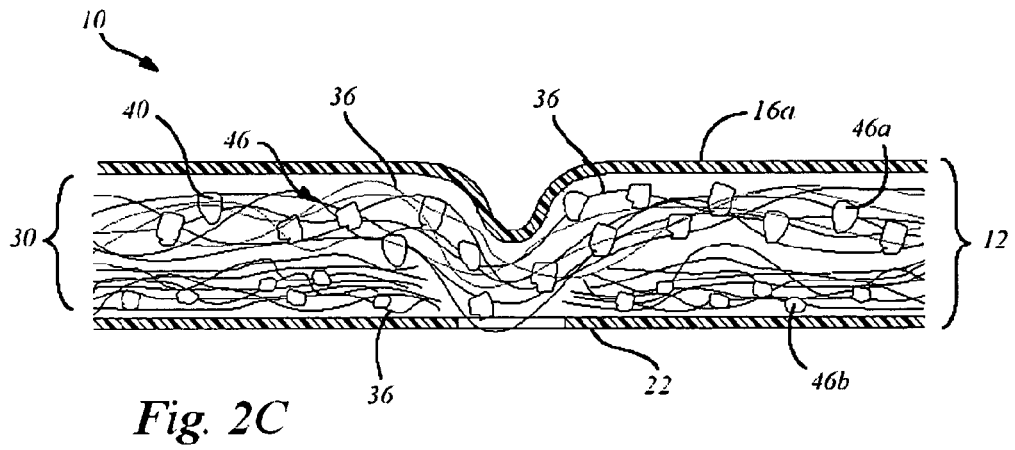
FIG. 2C is a cross-sectional side view of the sterilizeable, flexible laminate wound cartilage repair patch of the present invention, showing a lower and an upper layer both having a mechanical stabilizing feature in each layer.
Figure 2D:
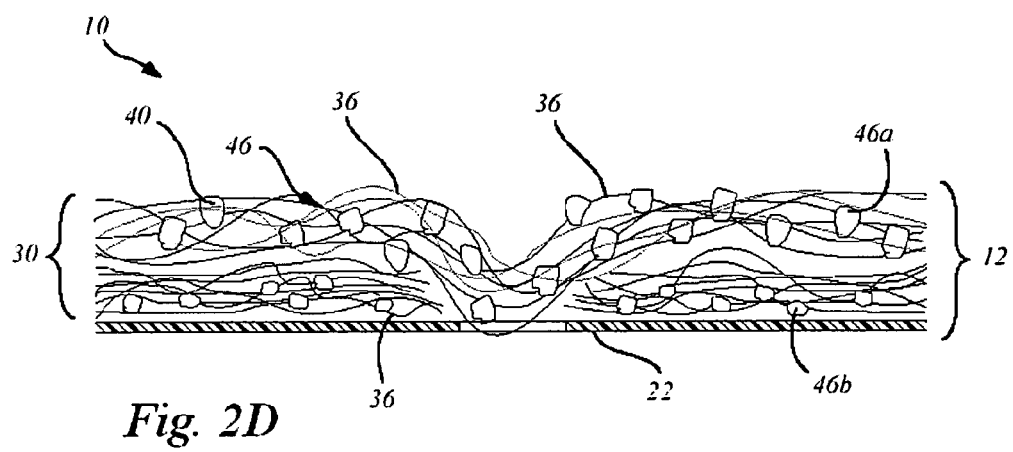
FIG. 2D is a cross-sectional side view of the sterilizeable, flexible laminate wound cartilage repair patch of the present invention, showing an embodiment having only a lower layer and with a mechanical stabilizing feature.
Figure 2E:
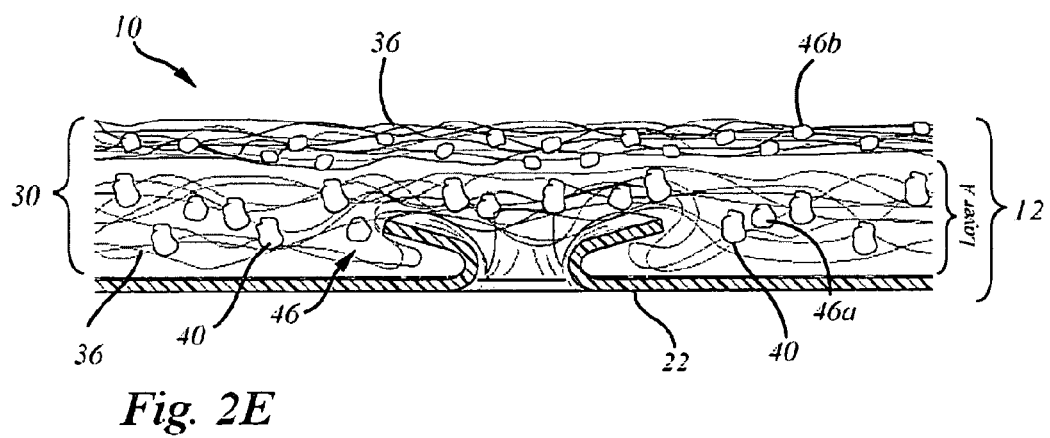
FIG. 2E is a cross-sectional side view of the sterilizeable, flexible laminate wound cartilage repair patch of the present invention, showing an embodiment wherein the lower layer has complex mechanical stabilizing features in it.

In a preferred embodiment, the matrix layer 30 is a sterile or sterilizeable, porous collagenous composite pad, interspersed with non-human collagen fibers 36 and natural Hyaluronic Acid fibers 40. The natural collagen is derived from a non-human source, such as porcine, bovine or vegetal collagen. The natural Hyaluronic Acid (HA) is derived from a natural non-mammalian source, such as via bacterial fermentation and via extraction from rooster combs. Other names for HA include: hyaluronic acid sodium salt, sodium hyaluronate, and hyaluronan. The natural HA can be provided in the matrix 30 in form of natural HA fibers 40 as shown in FIG. 2A, or as HA powder 40a in a gel or cream suspension 42 dispersed into the vacant spaces of the collagen fibers 36 as in FIG. 2B.

In the preferred embodiment, the composite cartilagenic matrix 30 also includes one or more tissue growth hormones (e.g., Somatotropine) and/or stimulators of growth factors 46. Growth factor stimulators are chemicals that enhance the expression of a growth factor at a given site. In the embodiment illustrated, the growth factor stimulators are Diacerein 46a and Rhein 46b. In the embodiment illustrated in FIG. 2B, the suspension 42 also contains Rhein 46b and/or Diacerein 46a. The weight range ratio of collagen to HA should be from about 0.1:99.9 to about 50:50 when the natural HA has a molecular weight of between 0.5 to 6 million Dalton. The Diacerein or Rhein concentrations should be in the range of about 10 to 50 micromolar added to the matrix in a powder form or as HA gel or cream containing the Diacerein or Rhein. Other compositions that are anticipated for inclusion in the matrix layer 30 include Chitosan compositions and Poly-Lactic Acid compositions.

Autologous mesenchymal stem cells 60 derived from a source external to the cartilage repair patch 10 diffuse into the patch 10 through the porous basement layer 22 and into the matrix layer 30 where they are supported by the fibrous components (collagen fibers 36 and/or HA fibers 40a) of the matrix 30. The matrix fibers 40 & 40a provide a support medium for the stem cells to grow and differentiate into chondrocytes. The exogenous growth factors 46, such as Diacerein down regulate inflammatory parameters (e.g., cytokines: IL-1, TNF-alpha, and free radicals) which contribute to inflammation and cartilage breakdown. Diacerein stimulates the production of certain growth factors, like TGF-β that additionally will stimulate production of cartilage components such as HA, collagen type-II, and proteoglycans (including aggrecans). Growth hormone will stimulate the production of cartilage and bone tissue. Further, endogenous growth factors 50 from an autologous serum fraction are added to the fibrin glue composition 54 stimulates differentiation of stem cells 60 in the blood clot/patch interface. The cumulative effect of these interactions leads to growth of hyaline-like cartilage.

Figure 3:
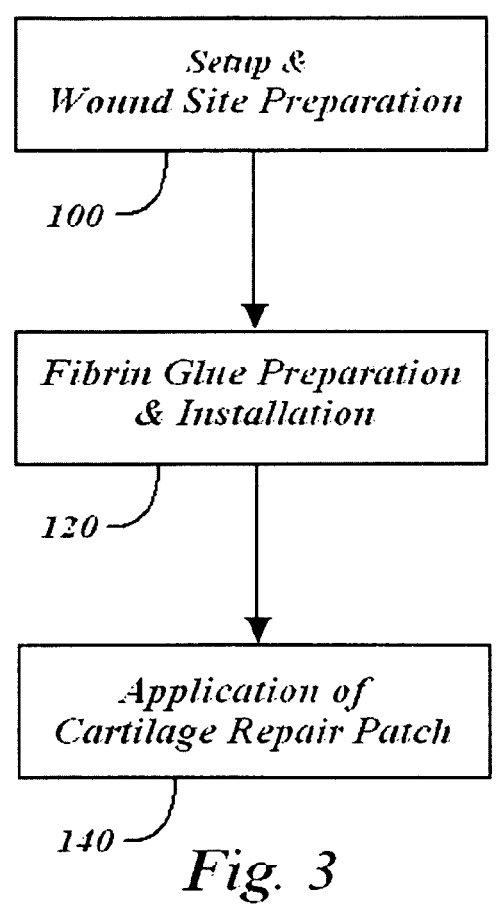
FIG. 3 is a generalized flow chart illustrating the main stages of the method of the present inventive system.

FIG. 3 is a generalized flow chart illustrating the main stages of the method of the present inventive system. In a preferred method of use, the present system comprises three stages: preparation of the wound site 100; preparation and installation of the fibrin glue 120; and application of the cartilage repair patch 140. In the first stage 100, as part of the set up, a blood sample is taken from the patient and an autologous serum fraction is obtained. The autologous serum fraction is used as a source of wound healing components, such as TGF-β1, and will be added at implantation within the fibrin-glue to the wound site 6. These endogenous components will enhance mesenchymal stem cell differentiation.

Figure 4A:
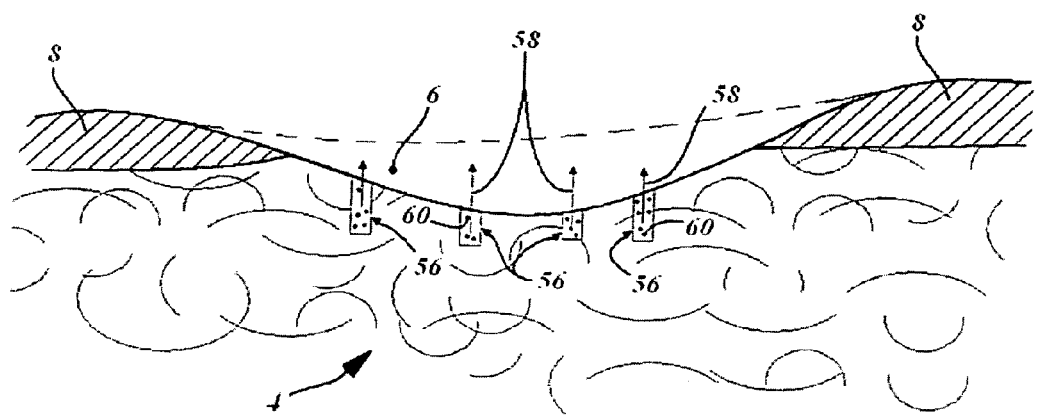
FIGS. 4A and 4B are cross-sectional views of a representative wound site and illustrate a first stage of preparation of the wound site to receive the present flexible laminate cartilage repair patch: (A) causing micro-fractures or perforations into the surface of the subchondral bone, and (B) forming a blood clot from local bleeding initiated by the causing of the micro-fractures.

Also in this stage, micro-fractures/perforations are made at the subchondral bone surface 14 to cause local bleeding 58 which perfuses the wound site 6 with fresh blood. See FIG. 4A. Causing local bleeding 58 at the subchondral bone surface 14 can be accomplished in a number of ways. In the preferred embodiment illustrated in FIG. 4B, the preparation of the existing chondral or osteochondral lesions is accomplished by causing micro-fractures or perforations 56 in the surface 14 of the subchondral bone 4—often associated with abrasion of sclerotic bone. As shown in the figure, the micro-fractures/perforations/abrasions 56 in the subchondral bone 4 causes bleeding 58 into the wound site 6. The blood 58 entering the wound site 6 contains autologous mesenchymal stem cells 60 and other healing components released by the subchondral bone 4 in response to the causing of the micro-fractures, perforations or abrasions 56.

Figure 4B:
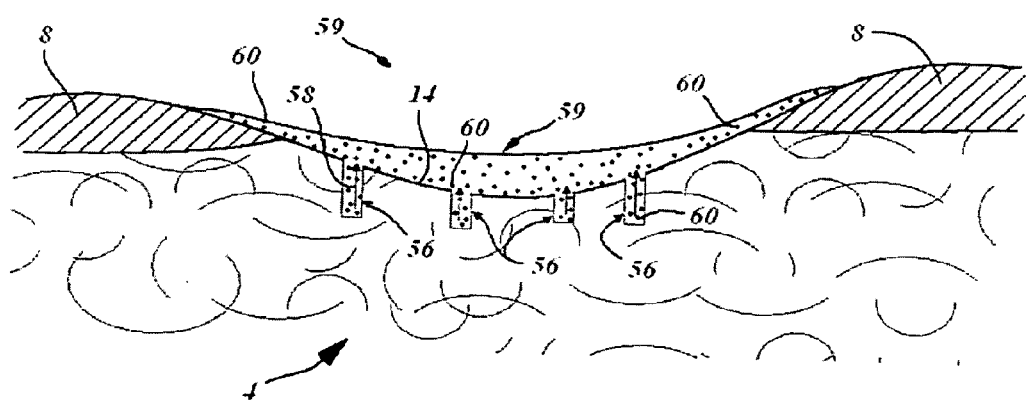

As shown in FIG. 4B, the blood 58 that perfuses the wound site 6 results in a blood clot 59 that forms at the site. The present system uses the micro-fracture technique to cause bleeding and stimulate release of autologous mesenchymal stem cells (MSCs) and growth factors into the clot 59. These pluripotential MSCs in the presence of the present cartilage repair patch 10 will differentiate into chondrocytes and produce extracellular hyaline-like cartilage matrix to repair/replace the existing chondral/osteo-chondral lesion 6.

Figure 5:
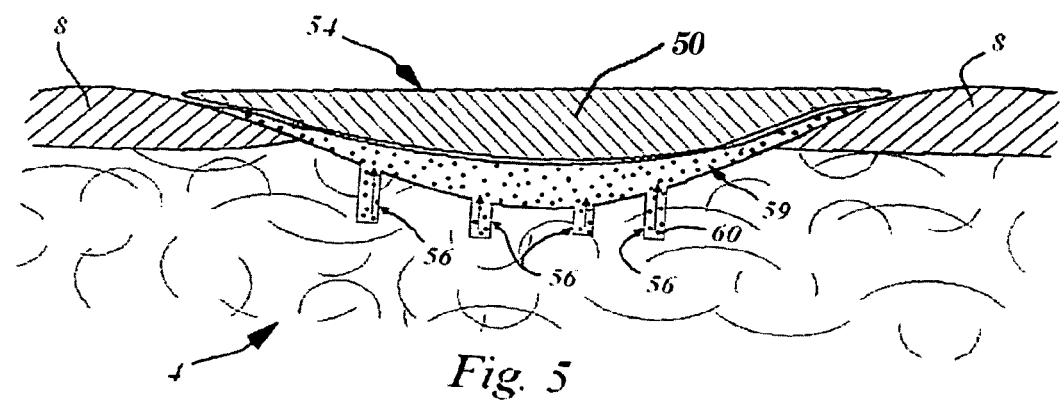
FIG. 5 is a cross-sectional view of a representative wound site and illustrates a step of the second stage of the present system: applying the autologous serum enhanced "fibrin glue" at the wound site.

After the wound site 6 is prepared, the second stage 120 of the method of the present system is accomplished. This stage 120 is the preparation and application of the fibrin glue 54 to the blood clot 59 at the wound site 6. As shown in FIG. 5, the fibrin glue 54 mingles with the fresh blood clot to form a blood clot/fibrin glue composite clot 54-59. However, other means of installing the fibrin glue 54 in place are known to and selectable by one of ordinary skill in the art for practice in the present system. For example, the cartilage repair patch 10 can be sutured in place (not shown).

Figure 6A:
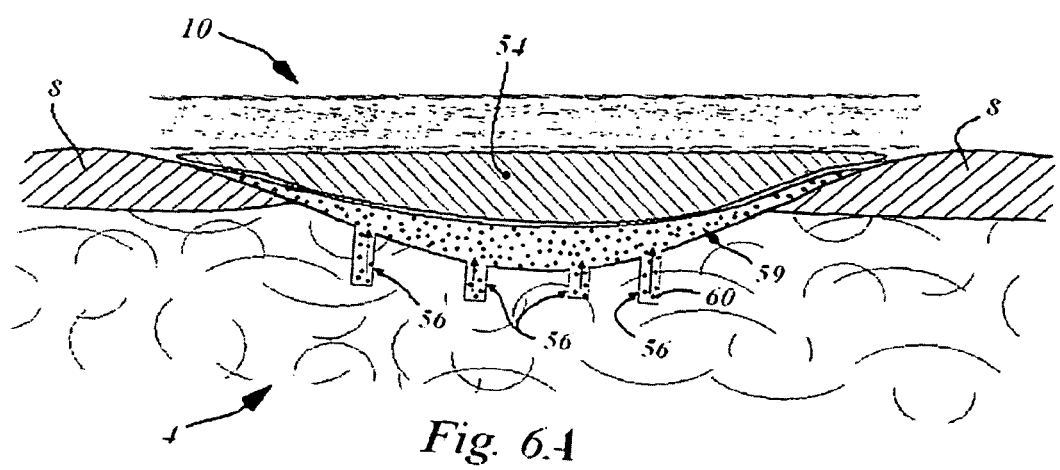
FIG. 6A is a cross-sectional view of a representative wound site and illustrates the placement of the flexible laminate cartilage repair patch to the wound site over a fibrin glue/blood clot.

After the fibrin glue 54 is applied in the wound site, the third stage 140 of the present method is then to be accomplished. This third stage 140 is the placement of the flexible laminate repair patch 10 to the wound site over the fibrin glue/blood clot composite 59/54 at the wound site 6. In FIG. 6A, the flexible laminate cartilage repair patch 10 is applied to the wound site 6. The fibrin glue 54 also may be freely applied after the repair patch 10 is in place to further accomplish adhering the repair patch 10 to the wound site 6.

Once this step is accomplished, the surgical stages of the present system are completed and the cartilage repair patch 10 continues healing purpose in situ.

Figure 6B:
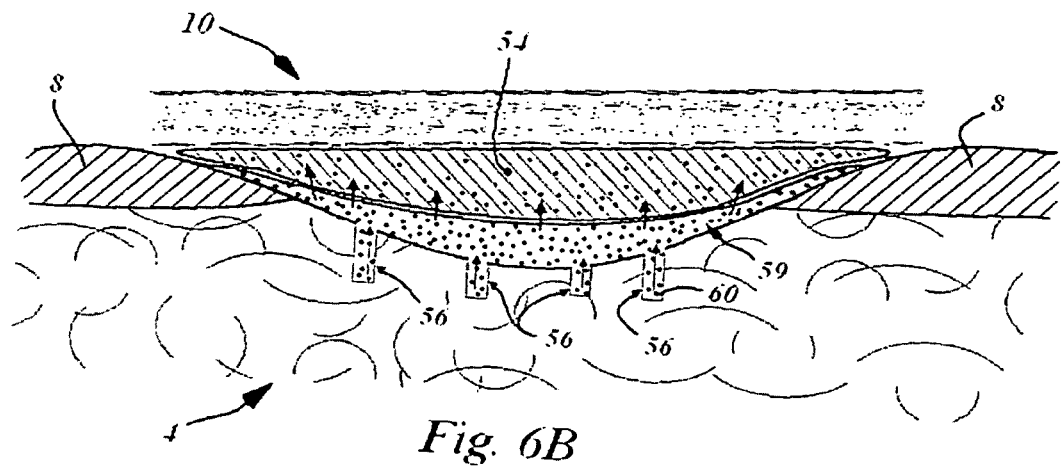
FIG. 6B is a cross-sectional view of a representative wound site and Illustrates the migration of Mesenchymal Stem Cells and other injury responsive blood components from the blood clot into the fibrin glue to form a blood clot/fibrin glue composite.
Figure 6C:
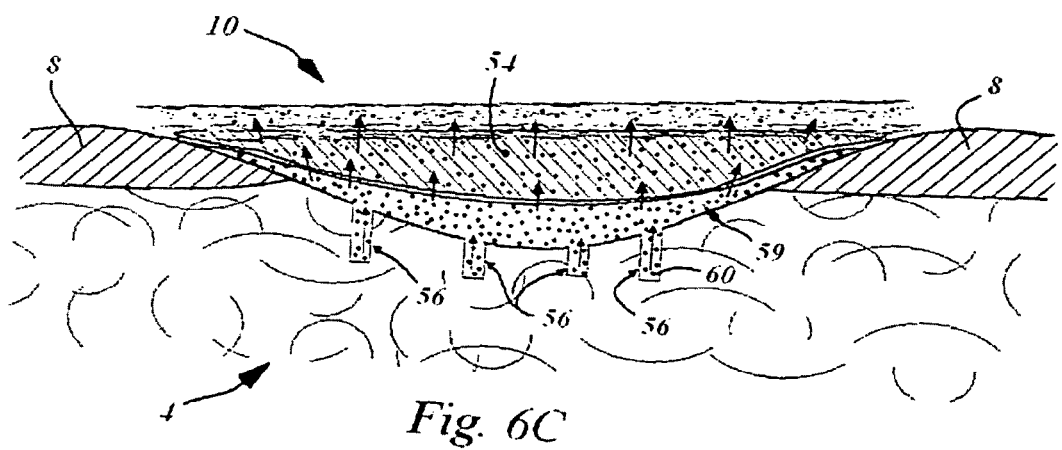
FIG. 6C is a cross-sectional view of a representative wound site and illustrates the migration of Mesenchymal Stem Cells and other injury responsive blood components from the blood clot/fibrin glue composite further still into the matrix of the cartilage repair patch.

As shown in FIG. 6B, Mesenchymal Stem Cells and other injury responsive blood components from the blood clot 59 migrate into the fibrin glue 54. FIG. 6C illustrates the further migration of the Mesenchymal Stem Cells and other injury responsive blood components from the fibrin glue/blood clot composite 54/59 continues through the porous outer layer 22 and into the matrix layer 30 of the cartilage repair patch 10. In the matrix layer 30, the mesenchymal stem cells and autologous growth factors interact with the constituents of the cartilage repair patch 10. The presence of these components results from their diffusion from the clot 59 into the cartilagenic matrix 30 of the cartilage repair patch 10. The occlusive layer 16 of the cartilage repair patch 10 prevents for a time the further diffusion of these different compositions into the joint space. Conversely, the mobile constituents of the matrix layer 30 can migrate out of the cartilage repair patch and into the mass of the fibrin clot 54, and further, into the blood clot 59 at the surface 14 of the subchrondral bone 4.

Figure 7:
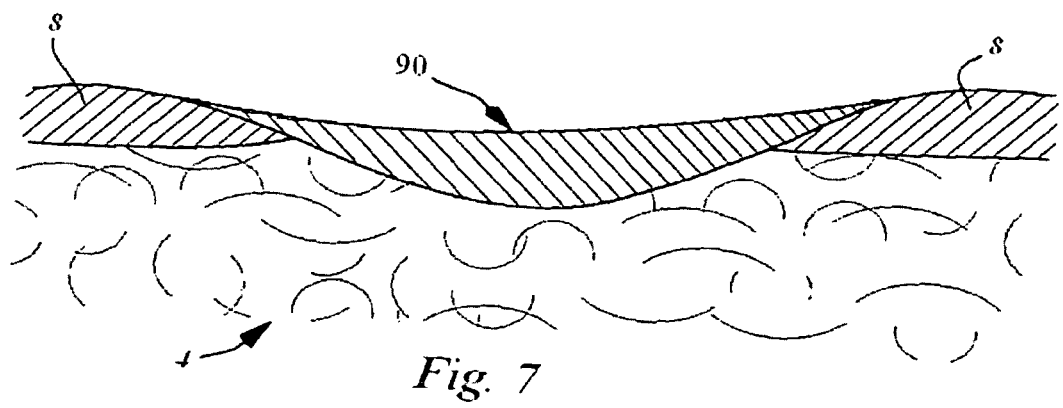
FIG. 7 is a cross-sectional view of a representative wound site and illustrates the resultant repaired site after the cartilage repair patch has been reabsorbed and the site transformed into bone and/or a hyaline-like cartilage.

The Diacerein 46a and the Rhein 46b inhibit the production and activity of inflammatory cytokines such as IL-1β, nitric oxide (NO), free radicals and matrix metalloproteinases all of which are involved in inflammation and cartilage destruction, particular in osteoarthritic joints. The Diacerein 46a and the Rhein 46b also stimulate the production of growth factors such as TGF-β which in turn stimulates expression of cartilage components such as hyaluronic acid, proteoglycans, aggrecans and collagenase II, all of which are important components of cartilage matrix. The growth hormone will also stimulate the growth of cartilage and bone tissue. Over time, as illustrated in FIG. 7, the cartilage repair patch 10 is reabsorbed and the defect site 6 is relatively rapidly transformed into a more physiologically hyaline-like cartilage 90.

The Collagen Cartilage Repair Patch

EXAMPLE

A collagen sheet 22 (XENODERM™—porcine type 1 and 2 collagen) was used for the lower layer 22. The Lower layer had mechanical properties to resist shear and pull stress and was resorbable in about 6 weeks. The collagen sheet 22 was put into a form, and then loaded with a collagen-HA suspension to which was added either a solution of Diacerein or Diacerein powder to obtain a concentration of 5-50 micromol. in dry-weight in patch after freeze-drying and sterilization. The result is a double layer collagen-pad with the lower layer to be disposed adjacent the bone surface. After manufacturing and before sterilization, the pads are put into a mechanical press to obtain a thickness of 0.5-2 mm. HA-concentration in the dry-frozen end product was in the range of about 0.1% to 2%. The HA is natural HA, that is, non-chemically modified HA, of fermentation origin.

In an advantage, a device and therapy is provided which better promotes regeneration of damaged joint cartilage.

In another advantage, a treatment and device for osteochondral injuries is provided that does not require cell culture.

In yet another advantage, a treatment and device for such injuries is provided that does not result in propagation of a fibrocartilaginous replacement tissue at the injury site.

In still another advantage, a treatment and device is provided which better insures that the resultant replacement tissue is appreciably representative of natural hyaline-like articular cartilage.

While the above description contains many specifics, these should not be construed as limitations on the scope of the invention, but rather as exemplifications of one or another preferred embodiment thereof. Many other variations are possible, which would be obvious to one skilled in the art. Accordingly, the scope of the invention should be determined by the scope of the appended claims and their equivalents, and not just by the embodiments.

The invention claimed is:

1. A laminate cartilage repair patch that is bio-compatible and physiologically absorbable for in situ cartilage repair in intra-articular lesions, comprising
    (1) a basement layer that is cell-porous and consists of sheet collagen; and
    (2) a cartilagenic matrix layer disposed on the basement layer, wherein the cartilagenic matrix layer is:
        a porous composite pad that consists of (a) collagen, (b) natural hyaluronic acid (HA), and (c) a chemical composition selected from the group consisting of natural hyaluronic acid (HA), Diacerein, Rhein, poly-lactic acid, somatotropine, and chitosan,
        wherein the porous composite pad is interspersed with non-human collagen fibers and said natural hyaluronic acid, and has embedded therein the chemical composition of (c);
    wherein the laminate cartilage repair patch is flexible.

2. The laminate cartilage repair patch of claim 1, wherein the collagen of the cartilagenic matrix is porcine, bovine or vegetal collagen.

3. The laminate cartilage repair patch of claim 1, wherein the sheet collagen is porcine type 1 and 2 collagen.

4. The laminate cartilage repair patch of claim 1, wherein the natural hyaluronic acid is in the form of fibers or a powder in a gel or cream suspension.

5. The laminate cartilage repair patch of claim 1, wherein the natural hyaluronic acid is a natural, non-human hyaluronic acid.

6. The laminate cartilage repair patch of claim 1, wherein the natural hyaluronic acid is a natural, non-human hyaluronic acid from a bacterial fermentation source.

7. The laminate cartilage repair patch of claim 1, wherein the chemical composition of (c) is selected from the group consisting of Diacerein, Rhein, poly-lactic acid, and chitosan.

8. The laminate cartilage repair patch of claim 1, further comprising an outer layer, wherein the cartilagenic matrix is disposed between the basement layer and the outer layer.

9. The laminate cartilage repair patch of claim 8, wherein the outer layer consists of sheet collagen.

10. The laminate cartilage repair patch of claim 9, wherein the sheet collagen of the outer layer or the outer layer and the basement layer is porcine type 1 and 2 collagen.

* * * * *